United States Patent
Teijido (10) Patent No.: US 9,301,682 B2
(45) Date of Patent: Apr. 5, 2016

(54) EYE EXAMINATION APPARATUS WITH DIGITAL IMAGE OUTPUT

(75) Inventor: Juan Manuel Teijido, Schliern (CH)

(73) Assignee: HAAG-STREIT AG, Koeniz (CH)

( * ) Notice: Subject to any disclaimer, the term of this patent is extended or adjusted under 35 U.S.C. 154(b) by 220 days.

(21) Appl. No.: 13/823,602

(22) PCT Filed: Aug. 18, 2011

(86) PCT No.: PCT/CH2011/000185
§ 371 (c)(1),
(2), (4) Date: Apr. 12, 2013

(87) PCT Pub. No.: WO2012/055050
PCT Pub. Date: May 3, 2012

(65) Prior Publication Data
US 2013/0286347 A1    Oct. 31, 2013

(30) Foreign Application Priority Data

Oct. 26, 2010   (EP) .................................... 10405203

(51) Int. Cl.
*A61B 3/14* (2006.01)
*A61B 3/00* (2006.01)
*A61B 3/13* (2006.01)
*A61B 3/135* (2006.01)

(52) U.S. Cl.
CPC ................. *A61B 3/14* (2013.01); *A61B 3/0083* (2013.01); *A61B 3/132* (2013.01); *A61B 3/135* (2013.01)

(58) Field of Classification Search
CPC ...... A61B 3/00; A61B 3/0008; A61B 3/0016; A61B 3/0025; A61B 3/0033; A61B 3/0041; A61B 3/0005; A61B 3/0058; A61B 3/0091; A61B 3/10; A61B 3/13; A61B 3/132; A61B 3/135
See application file for complete search history.

(56) References Cited

U.S. PATENT DOCUMENTS

| | | | |
|---|---|---|---|
| 5,250,966 A | 10/1993 | Oda et al. | |
| 5,701,197 A | 12/1997 | Yano | |
| 5,912,720 A | 6/1999 | Berger et al. | |
| 5,914,770 A | 6/1999 | Bergner et al. | |

(Continued)

FOREIGN PATENT DOCUMENTS

| | | | |
|---|---|---|---|
| DE | 37 37 935 A1 | 5/1989 | |
| DE | 195 41 477 A1 | 5/1996 | |

(Continued)

OTHER PUBLICATIONS

Japanese Office Action dated May 21, 2015 issued in related JP Application No. 2013-535226 with an English translation.

*Primary Examiner* — Scott J Sugarman
*Assistant Examiner* — Robert E Tallman
(74) *Attorney, Agent, or Firm* — Birch, Stewart, Kolasch & Birch, LLP (57) ABSTRACT

A device for stereoscopic examination of an eye, in particular a slit-lamp microscope, comprises, according to a first aspect of the invention, a lens for generating two images of the eye, wherein the device comprises at least one image sensor for electronic recording of the two images. According to a second aspect of the invention, the device for examination of an eye, in particular the slit-lamp microscope, comprises a lens for generating one image, wherein it comprises an image sensor for electronic recording of one image, and a viewing unit with an image-reproducing unit for presenting the image, and an eyepiece for viewing the image.

17 Claims, 4 Drawing Sheets

(56) References Cited

U.S. PATENT DOCUMENTS

| | | | |
|---|---|---|---|
| 2003/0071893 A1* | 4/2003 | Miller et al. | 348/42 |
| 2005/0018134 A1* | 1/2005 | Noda et al. | 351/205 |
| 2005/0195359 A1* | 9/2005 | Makino | 351/200 |
| 2009/0263115 A1 | 10/2009 | Suzuki et al. | |
| 2010/0201799 A1 | 8/2010 | Mohrholz et al. | |
| 2010/0259820 A1* | 10/2010 | Nakamura et al. | 359/466 |
| 2011/0234977 A1* | 9/2011 | Verdooner | 351/207 |

FOREIGN PATENT DOCUMENTS

| | | |
|---|---|---|
| DE | 197 20 851 A1 | 11/1998 |
| EP | 1 908 399 A1 | 4/2008 |
| JP | 4-336031 A | 11/1992 |
| JP | 5-245109 A | 9/1993 |
| JP | 2004-361891 A | 12/2004 |
| JP | 2006-303832 A | 11/2006 |
| WO | WO 2006/000072 A1 | 1/2006 |
| WO | WO 2009/043494 A1 | 4/2009 |

* cited by examiner

EYE EXAMINATION APPARATUS WITH DIGITAL IMAGE OUTPUT

TECHNICAL FIELD

The invention relates to a device for examining an eye, having an optical unit for generating an image of the eye.

PRIOR ART

Slit-lamp microscopes are ophthalmological examination instruments, by means of which the eyes can be examined in monoscopic or stereoscopic fashion. For the purpose of stereoscopically observing an eye, known slit-lamp microscopes have an optical unit for generating two images of an eye and two eyepieces for stereoscopically observing the images, and also an illumination unit. The illumination unit is arranged on a vertically extending branch of a holder unit. The eye to be observed can be positioned in a plane extending approximately horizontally on one side of the holder unit. The illumination unit comprises an incandescent lamp, LEDs or similar illumination means for a slit illumination.

Current devices for examining and/or treating an eye comprise a digital camera for recording an image and a screen for rendering the image.

A disadvantage of these devices is that the coordination is unfamiliar to the examining person when operating the device and at the same time observing the image material on the screen. Furthermore, the observation via a screen during the examination is not optimal because the screen must have a certain distance from the observer so that the observer can easily and quickly focus on the screen. In almost every case, the positioning is inexpedient for the examining person and the examined person, and for design reasons.

DESCRIPTION OF THE INVENTION

It is an object of the invention to develop a device for stereoscopically examining an eye, which is part of the technical field mentioned at the outset and which is more ergonomic and enables improved operation.

The solution to the object is defined by the features of claim 1. According to a first aspect of the invention, the device comprises at least one, preferably two image sensors for electronic capture of the two images.

This renders it possible to process the image material, in particular for stereoscopically observing. The image sensor can in each case capture a so-called half-image, by means of which a three-dimensional representation can be obtained. A half-image in each case typically represents the view of an object by one eye, i.e. the two half-images display substantially the same object from two different viewing angles. As a result of this, the image material can subsequently, or else substantially in real time, be processed electronically. Here, processing can comprise very different, in particular known, image and film processing techniques. Mentioned here as examples are the contrast, brightness, color, auxiliary lines (grids, etc.), abstraction of the image material, image superposition (for comparing two images or precisely for the stereoscopic display thereof) etc.

The device for stereoscopically examining an eye (referred to as device below), in particular the slit-lamp microscope, can have a largely conventional design, i.e. be designed in a known fashion.

According to a first aspect of the invention, the optical unit comprises two lenses, which can focus on the same point from different angles such that a stereoscopic image can be obtained from the two image data sets. The lens system of the lenses can be matched specifically to the image sensor or sensors, as a result of which they can, in certain circumstances, differ from conventional lenses of a slit lamp. A person skilled in the art knows how the corresponding optical unit for generating two images of the eye for the subsequent stereoscopic observation can be embodied.

The image sensor can be designed to be sufficiently large for it to be possible, thereon, to record the two images next to one another at the same time. The image sensor can also record the two half-images alternately in time, particularly if the sensor can process individual images with a sufficiently high frequency, e.g. greater than or equal to 100 Hz. However, a disadvantage may arise as a result of the fact that only half the image frequency can be obtained using the same image sensor. In the case of rapid eye movements of the observed eye, the image pairs may, as a result thereof, not be matched sufficiently well to one another or not have a sufficient degree of synchronicity for the purposes of stereoscopic observation, and so the quality of the 3D effect during the observation may be too low. However, depending on the recording frequency attained by the image sensor, this may nevertheless be accepted, particularly if this allows for a more compact design of the device. In a further preferred variant, provision is made for an interlace technique, in which the pixel sensors record the left and the right half-image, alternating line-by-line. To this end, the pixel lines can alternately be embodied in such a way that, for example by means of suitable lens elements, a light ray is only captured by a first pixel line if it has a specific angle of incidence $\alpha$, while a second pixel line only captures a light ray if it has an angle of incidence $\beta \neq \alpha$, as a result of which it is possible to keep the two half-images apart.

In a further preferred embodiment, the device for the left and for the right image respectively comprises its own image sensor or image sensor area, and so the maximum possible image frequency of the image sensor can be utilized.

The device as per the first aspect of the invention can be embodied in such a way that an image can be captured by the sensor and can, at the same time, be observed as an analog image by means of a conventional eyepiece. By way of example, a beam splitter may be provided in the device to this end, wherein a partial beam can be routed from the eye to be examined to the eyepiece and a further partial beam can be routed to the sensor. The optical unit for generating the images can, particularly in the case where no analog observation option is provided, be matched to or optimized in respect of the image sensor.

The image sensor or the optoelectronic sensor can be embodied as a CCD (charge coupled device) sensor, CMOS (complementary metal oxide semiconductor) sensor, DPS (digital pixel sensor) sensor, or else as an image sensor for other spectral regions. A person skilled in the art is well aware of further suitable devices for electronic capture of image material or film material. Finally, it is also possible for provision to be made for more than two image sensors. By way of example, provision can be made for two different image-sensor types for different spectral regions such that, overall, four image sensors are present.

The device preferably comprises an observation unit with two image rendering units for displaying the two images and two eyepieces for stereoscopically observing the images. The observation unit is preferably connected to the image sensor via a data line in such a way that the images recorded electronically by the image sensor can be transmitted to the observation unit in the form of electronic data. Within the observation unit, the image data are preferably sent to two image rendering units. The image rendering units receive the image data and convert these into an image visible for the observer. To this end, the image rendering units are preferably embodied as electronic screens, in particular as two micro-screens. The screens can be embodied as known t-LCDs (transmissive liquid crystal displays), LCoSs (liquid crystal on silicon), OLEDs (organic light-emitting diode) or as optical MEMSs (micro-electromechanical system). The image rendering units are preferably observed through respectively one eyepiece, in particular through respectively one eyepiece for the right eye and for the left eye. The observer can thus observe the two images stereoscopically, i.e. as a three-dimensional image, through the two eyepieces.

The provision of the two eyepieces for stereoscopically observing the two images renders it possible that the device per se is available in a known form familiar to the user. Moreover, this form of the stereoscopic display of recorded image material constitutes a particularly simple variant, particularly because the observer does not need to re-accustom himself from conventional devices for stereoscopically observing an eye.

The eyepieces can comprise a lens element or a lens system. Depending on the embodiment of the image rendering unit, the eyepieces can also merely be embodied as a tube jacket, which optionally comprises a viewing glass for protecting the image rendering unit and/or a magnifying glass for magnifying the image displayed by the image rendering unit.

In some variants, it is also possible to dispense with the eyepieces, wherein use is made of alternative observation units. By way of example, use can be made of an autostereoscopic display. Furthermore, a projection by means of two projectors, more particularly by means of beamers, and the use of polarization filters is also feasible. The observation unit can also merely have one image rendering unit, on which, for example, imaging takes place by means of anaglyph methods and the stereoscopic image thereon is observed by means of appropriate glasses. Although this can cut down on one screen, the color fidelity is lost. In this respect, a person skilled in the art is also aware of further techniques.

The observation unit is preferably embodied to be movable independently of the optical unit. The observation unit, in particular the eyepieces and the image rendering units, is preferably embodied in such a way that it can pivot about a vertical axis relative to the optical unit or the lenses. The image rendering unit can be mounted in pivotable fashion about the same axis as the optical unit. This results in a plurality of usage options of the device.

In a first variant, the observation unit can be fixed with respect to the eye to be observed, for example by means of a latching device, while the optical unit remains pivotable independently of the observation unit. As a result, the observer can observe the eye and change the observation angle with respect to the eye, without it being necessary to move the observation unit. As a result, a more ergonomic examination is made possible for the observer.

In a second variant, the observation unit can, for example, be reversibly coupled to the optical unit. As a result, the movements of the optical unit and the image rendering unit can, if so desired by the observer, be coupled in the conventional manner, which can, for example, be achieved by means of a known mechanical coupling device, like, for example, an interlocking connection and/or force fit between the two pivot axes, between the optical unit and the image rendering unit.

In a third variant, both the observation unit and the optical unit can be moved independently. This can be advantageous if there are two observers (e.g. trainer and trainee) and one wishes to pass the observation unit to the other. This is because there is no need to swap positions in this case. The optical unit can remain fixed while the observation unit is pivoted.

In a fourth variant, the observation unit, which substantially comprises the eyepieces with the micro-screens, can be completely detached from the microscope or the optical unit. By way of example, such an observation unit can find use in telemedicine or for training purposes. The observation unit can comprise an interface, by means of which the former can be connected directly to a slit lamp according to the invention, indirectly to a slit lamp according to the invention via a computer or only to a computer which has appropriate image data material available. The observation unit can furthermore be connected directly or indirectly to the Internet or any other network, and so data, in particular image data, can be acquired from the network. In one application, an ophthalmologist can examine a patient using a digital slit lamp, while an expert, located at some distance, can also observe or even influence the examination by means of a detached observation unit. In a further application, every trainee can be provided with a detached observation unit during practical training for the schooling for operating a slit lamp, with each observation unit being connected to a digital slit lamp which is being operated by the instructor. As a result, the trainees can also observe an examination of an eye online under conditions similar to in practice. A person skilled in the art knows that all applications can also be carried out by complete digital slit lamps, but that, depending on use, the use of detached observation units may be advantageous for reasons of costs and/or space because this substantially makes it possible to dispense with the expensive microscope.

The observation unit can also be embodied as 3D video glasses, i.e. as glasses which comprise two integrated screens. These can be connected to the image sensor via cables or in a wireless fashion. By way of example, the 3D video glasses can be held detachably in the device, and so the observer can optionally remove the 3D video glasses from the holder and put them on, or leave them in the holder and observe the image material in a conventional fashion. The device can also support the use of a plurality of 3D video glasses. This can be used, for example, to carry out training.

In some variants the observation unit can also be mounted in a fixed fashion relative to the optical unit. As a result thereof, the observer does not need to re-accustom himself from the conventional devices.

The device preferably comprises a data processing unit. The data processing unit preferably comprises a processor for processing data, in particular the electronically captured images, and a storage device for storing the data, in particular the electronically captured and/or the processed images. This renders it possible that the images captured by the image sensor can be processed electronically by the image rendering unit before or during the display for better pathological examination. Processing the data, in particular the electronically captured image data, preferably comprises known image and/or film processing techniques. Here, electronic processing can comprise image optimization, within the scope of which, for example, the contrast can be improved, the colors can be changed, the brightness can be influenced, the image can be abstracted (for example to reproduce contours) etc. Furthermore, this can also be used to calculate a schematic three-dimensional eye by incorporating data from other measurement methods. Finally, it is also possible to calculate and display a residual image of an ideal eye or to simulate a surgical intervention. A person skilled in the art knows that data processing makes it possible to process the image data in a nearly unrestricted fashion, in particular that the list above is not exhaustive.

There furthermore is the possibility that the image data from a patient can also, in his absence, be recalled from the storage device and be observed. This can, for example, be advantageous if the examining person wishes to obtain a second opinion in the absence of the patient. The storage device can store the raw data and/or the processed image data. The processor can have a known design and be acquired from various manufacturers. Naturally, the data need not be exclusively image data.

In some variants, the data processing unit can also have a simpler design such that image processing is not possible or only possible to a limited extent. In particular, this can be sufficient if the device has an interface to an external data processing device (computer, laptop or the like), by means of which the data can be processed and stored.

The device preferably comprises an interface for transmitting data to an electronic instrument and for receiving data therefrom. As a result, it is possible to send the image data to a third person (e.g. a medical practitioner) or to hand it to a patient on a data medium or as a printout. As a result of the fact that data can also be received, it is possible to receive image data or else further data, such as settings of the device, from an examination and to observe these on the dedicated device. In the case of a real-time transmission, this allows an eye of a patient to be examined at one device, with further persons being able to follow this examination in real time. This can be of interest within the scope of training in particular. Here, the interface can be embodied as a data line, as a wireless connection (radio, infrared, Bluetooth, etc.) or as a further interface known to a person skilled in the art. In particular, it is also possible to provide a plurality of interfaces, in particular different types of interfaces.

Alternatively, it is also possible to dispense with this interface, particularly if the device itself for example comprises a computer and/or an interchangeable storage medium (memory stick, disk, hard disk, etc.).

The electronic instrument is preferably embodied as one or more of the following instruments:
 a second device for stereoscopically examining an eye, in particular a slit lamp;
 a computer or a laptop, in particular a computer network;
 a screen, in particular a screen for stereoscopically observing the images, preferably an autostereoscopic display for stereoscopic rendering of the image material;
 a PDA (personal digital assistant), iPad or the like;
 a mass storage device, e.g. an external hard disk.

One or more projectors (respectively for one half-image) or a display, in particular a conventional screen, television or flat screen, by means of which the image data can be displayed, can be connected directly or indirectly to the device, e.g. via a computer. The image data can be displayed two-dimensionally by means of one screen by virtue of only one of the two images being displayed. Alternatively, the image data from the two images can be converted into an anaglyph image, in particular a color anaglyph image, and displayed on the screen such that the image material can be observed as a three-dimensional representation by means of suitable glasses. Naturally, it is also possible to use an autostereoscopic display for this purpose. Furthermore, use can also be made of shutter glasses, wherein the screen alternately displays the half-images at a high frequency and, synchronously therewith, the shutter glasses in each case cover one eye. It is also feasible to project the two half-images through polarization filters onto a surface containing the polarization plane in the case of light reflection, with the observer putting on corresponding polarization glasses. Furthermore, the device can be connected using cables or in a wireless fashion, directly or indirectly, to 3D video glasses, with the 3D video glasses themselves comprising two micro-screens. A person skilled in the art is well aware of further display options for three-dimensional images. The image data can be observed via a display or a projector, both in real time and at a later stage.

If the device is connected to a computer via a data channel, the data can naturally be transferred directly from the computer to further known electronic devices, such as e.g. a PDA, a memory stick, a CD, a DVD, a blu-ray disk, a hard disk, in particular an external hard disk, etc. However, in a further advantageous embodiment of the device, the device itself comprises an interface by means of which one or more of the aforementioned electronic devices or further devices known to a person skilled in the art can be directly connected for data interchange. A USB connector of any type is mentioned here in exemplary fashion. By way of example, it is possible to load an operating system into the image rendering unit, by means of which operating system the data can be managed. A control instrument of the device, for example the joystick for operating the cross slide, can to this end assume the function of the mouse in a separate setting, and so a cursor can be guided on the micro-displays of the image rendering unit. The data can also be stored automatically on a conventional storage medium.

A person skilled in the art is also well aware of further instruments which can be connected to the device via a data channel. These also comprise further examination instruments, such as e.g. a tonometer or the like. As a result, it is possible to combine the data established by the various measurement methods.

The interface can preferably be used to receive electronically captured images from the second device for the purpose of stereoscopically examining an eye, and these images can be rendered by means of the image rendering unit. The second device for stereoscopically examining an eye is preferably likewise equipped with an image rendering unit with electronic screens. As a result, it is possible, for example for training purposes, to send the image material between the devices and to observe it by means of the device. Furthermore, it is also possible to send setting data of the device (lamp settings, gap dimensions, etc.), which setting data can be set either manually or automatically. It is also possible to identify the devices (data was sent by slit lamp XY) by means of the transmittable data.

The data are not necessarily sent directly to a device for stereoscopically examining an eye, but can also be sent to such a device via a computer or a computer network, with it optionally being possible for the data to be processed in advance by means of a computer. In particular, the devices can be connected by a conventional network. Of course, it is not mandatory for a further device such as this to be connected to the computer or to the computer network.

The data preferably comprise electronically captured images, time, date and/or setting data of the device. The setting data preferably furthermore comprise the slit width, the slit height, utilized filter types, the exposure method and/or the magnification factor. By way of example, date and time can be automatically linked to the image data in order to simplify retrieval.

A person skilled in the art knows that it is not necessary for all the above-listed data types to be provided for transmission.

The images can, by means of the observation unit, preferably be selectively rendered statically as an image, dynamically as a film or dynamically as a film in real time. The device can be designed such that, during observation, an image can also be "frozen" for the purpose of static observation. Stored image material can also be subsequently loaded by means of a correspondingly equipped slit lamp, for example, and observed statically as images or dynamically as film recording.

In a second aspect of the invention, a device for examining an eye, in particular a slit-lamp microscope, preferably comprises an optical unit for generating an image, an image sensor for electronically capturing an image and an observation unit with an image rendering unit for displaying the image, and also an eyepiece for observing the image.

In this context, a person skilled in the art knows that the aforementioned preferred features can likewise be combined with the second aspect of the invention, except for those features which necessarily relate to the stereoscopic application.

Further advantageous embodiments and feature combinations of the invention emerge from the following detailed description and from the entirety of the patent claims.

BRIEF DESCRIPTION OF THE DRAWINGS

In the drawings used to explain the exemplary embodiment.

In principle, the same parts have been provided with the same reference signs in the figures.

WAYS OF IMPLEMENTING THE INVENTION

The term light ray used in the following text should not be understood as being restricted to a single light ray or to a photon; rather, it should also be understood to mean a light wave beam, which can represent an image.

Figure 1:
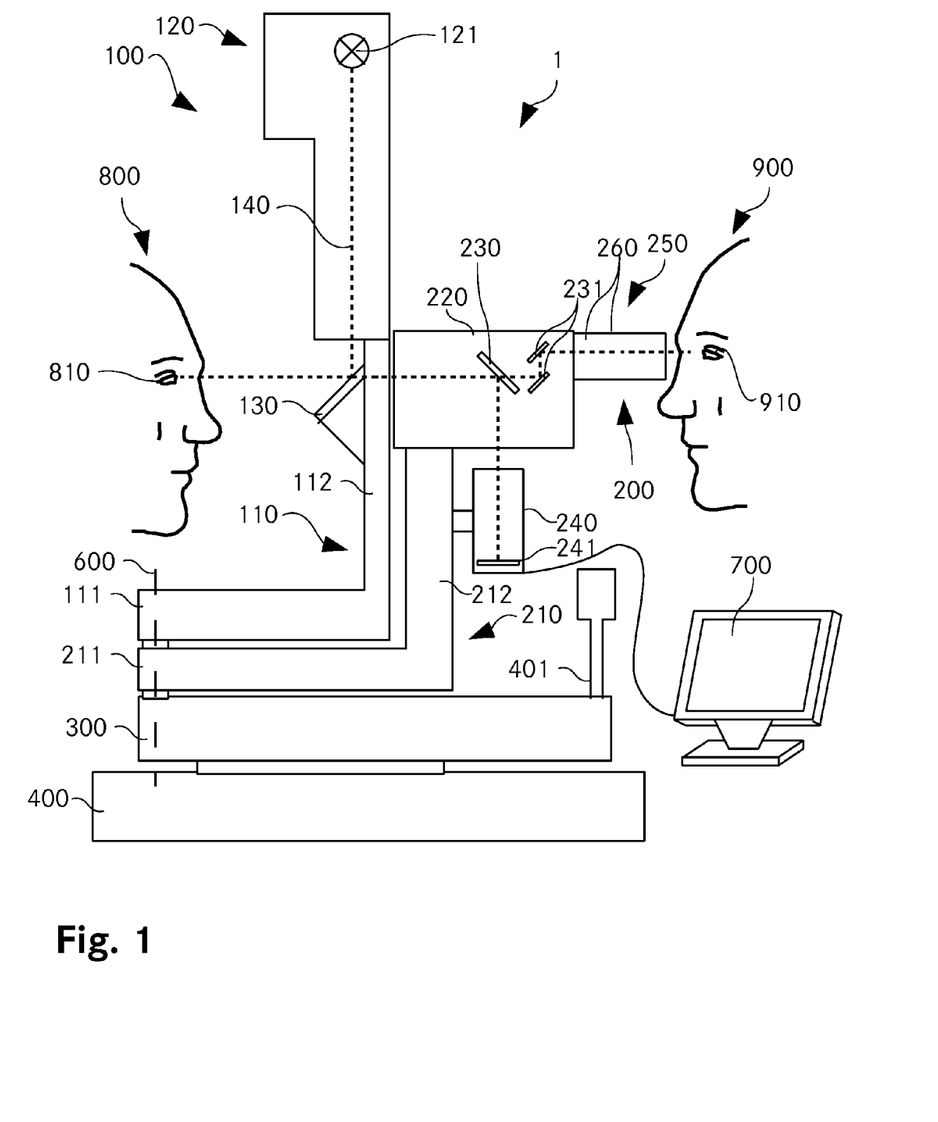
FIG. 1 shows a schematic illustration of a side view of a first embodiment of a device for examining an eye.

FIG. 1 shows a device 1 for examining an eye, embodied as a slit lamp 1. The slit lamp 1 comprises an illumination unit 100, an optics part 220, an observation unit 200 which are mounted on a cross slide 300.

The cross slide 300 itself is mounted on a base plate 400, which can be embodied as a tabletop, and can be displaced in the x-, y- and z-directions. The slide 300 can be controlled by means of an operating element 401, which is arranged on same. Using this, the illumination unit 100 and the observation unit 200 can be displaced over the slide 300; said units are also arranged in mutually independently pivotable fashion about a common axis of rotation 600.

The illumination unit 100 comprises an L-shaped element 110 with a horizontal section 111 and a vertical section 112. In a distal region of the horizontal section 111, the L-shaped element 110 comprises a vertically oriented axis of rotation 600. An illumination device 120, comprising a light source 121, is arranged at the top of the vertical section. The illumination unit 100 is designed in such a way that it is possible to generate a defined light strip, which can be projected onto an eye 810. On the inner side of the L-shaped element 110, on the vertical section 112, there is a mirror 130, which is inclined at an angle of 45° with respect to the vertical section 112. A light ray 140 generated by the light source 121 is routed vertically downward onto the mirror 130 arranged at a 45° angle and from there it is routed to the eye 810 of the patient 800.

The embodiment shown in FIG. 1 comprises an L-shaped element 210 with a horizontal section 211 and a vertical section 212. The L-shaped element 210 is mounted on the axis of rotation 600 in a distal region of the horizontal section 211 and below the horizontal section 111 of the L-shaped element 110. The two L-shaped elements 110, 210 are thereby effectively stacked on top of one another and have a common axis of rotation 600. An optics part 220 is arranged at the top, on the vertical section 212, and the light rays 140 reflected by the eye 810 reach the former. The optics part 220 is substantially embodied as a biomicroscope, which can record two half-images of a stereoscopic image. However, in the present embodiment, the optics part 220 comprises two semi-transparent mirrors 230, which, in the direction of the light rays 140 reflected by the eye 810, are tilted downward at an angle of 45°. These semi-transparent mirrors 230 are used to split the light rays reflected by the eye 810 into respectively two partial beams.

In each case, one partial beam is routed downward into an image recording unit 240. The image recording unit 240 comprises two image sensors 241 for electronic capture of the images represented by the two partial beams. The image recording unit 240 can also comprise further components such as e.g. a lens system, a diaphragm, etc. The image sensors 241 are connected to a screen 700 via a data channel. The screen 700 can be used to display the image data from the image sensors 241 in three dimensions by means of known techniques (anaglyph method, autostereoscopic display, etc.). This data can naturally also be displayed two-dimensionally. A data processing device (not illustrated here) is provided for processing the image data.

The two further partial beams are, via two deflection mirrors 231 which can also be realized as prisms, respectively routed into one eyepiece 260 of an image rendering unit 250, as a result of which the images can also be observed in an analog fashion, in particular in the "well-established" form, by an examining person 900.

More detailed illustrations of the optical components, in particular of lens systems for magnification and focusing, filters etc., have deliberately been dispensed with because a person skilled in the art is sufficiently well aware of the design thereof.

Figure 2:
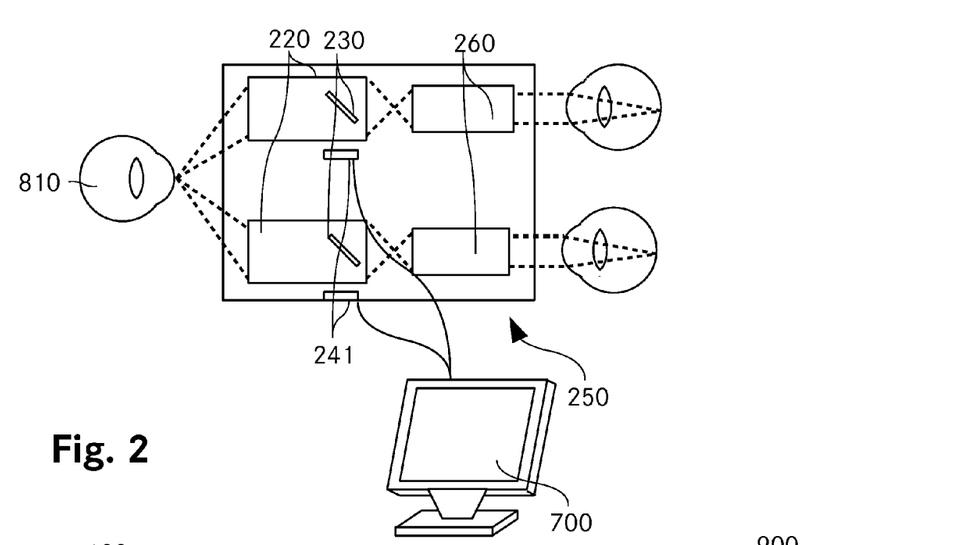
FIG. 2 shows a simplified sectional illustration through the optical unit and the image rendering unit of a device according to the invention for stereoscopically examining an eye.

FIG. 2 shows a simplified schematic illustration of the beam path as per FIG. 1. The light rays reflected by the eye 810, which respectively comprise a left half-image and a right half-image, which in combination render possible a stereoscopic representation, respectively reach an optics part 220, which can in each case comprise a lens system (not illustrated), as far as the semi-transparent mirror 230. The latter, as described above, respectively divides the light rays into two partial beams, with respectively one partial beam being routed to the image sensors 241 and the second partial beam respectively being routed through the semi-transparent mirror 230 into the eyepieces 260 of the observation unit 250. The examining person 900 can use the eyepieces 260 to observe the images directly and in an analog stereoscopic fashion. The image sensors 241 are connected via data channels to a screen 700, by means of which an examining person 900 can observe the image material in digitally processed form or as raw data. In some variants, the eyepieces can also be replaced by image sensors, as a result of which it is possible to dispense with the semi-transparent mirrors 230. Furthermore, the eyepieces 260 can be equipped with micro-screens which are connected to the image sensors 241, wherein non-transparent or completely reflecting mirrors are used in this case instead of the semi-transparent mirrors 230 (see below).

Figure 3:
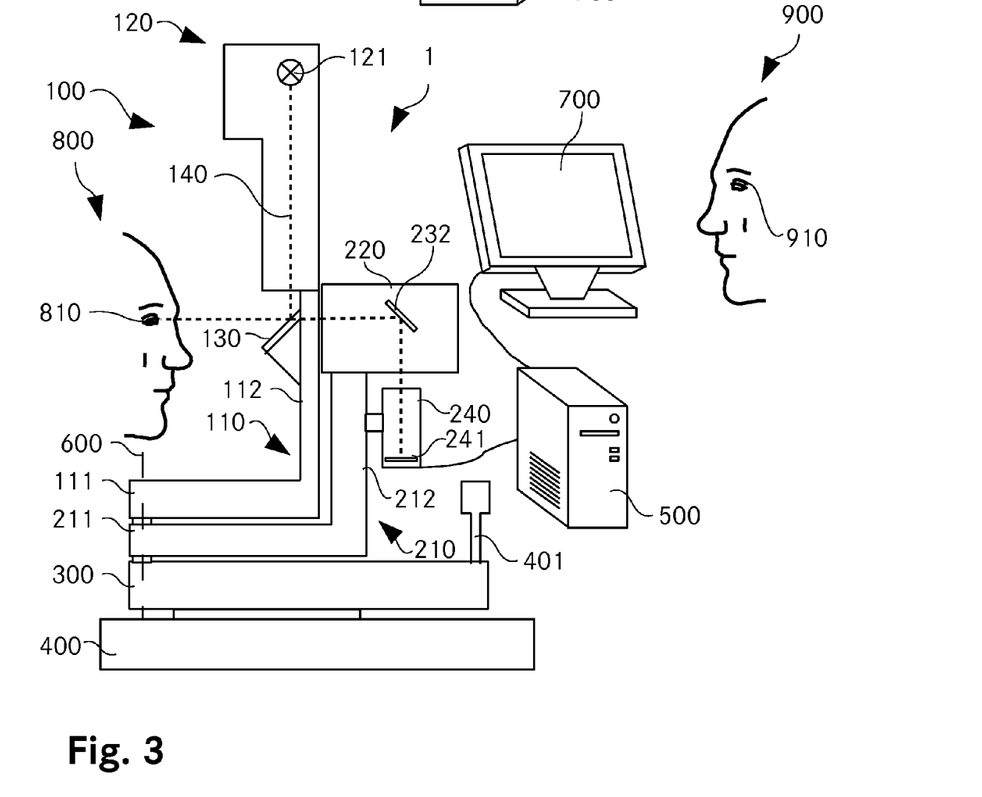
FIG. 3 shows a second embodiment of a device according to the invention as per a first aspect of the invention.

FIG. 3 substantially shows the device as per FIG. 1, wherein, as mentioned above, the semi-transparent mirrors 230 from FIG. 2 have been replaced by mirrors 232 which are non-transparent, as result of which the eyepieces 260 are also obsolete and thus not provided in this embodiment. The image data, which represent the two half-images, are sent from the two image sensors 241 to a computer 500 in the present embodiment. In FIG. 2, this is illustrated by means of a cable, but a wireless transmission is also feasible. The computer 500 can be used to store and process the image data and make them available to further users by means of, for example, a network (not illustrated). The computer 500 in turn is connected to a screen 250, by means of which the image data can be displayed either two-dimensionally or three-dimensionally.

Figure 4:
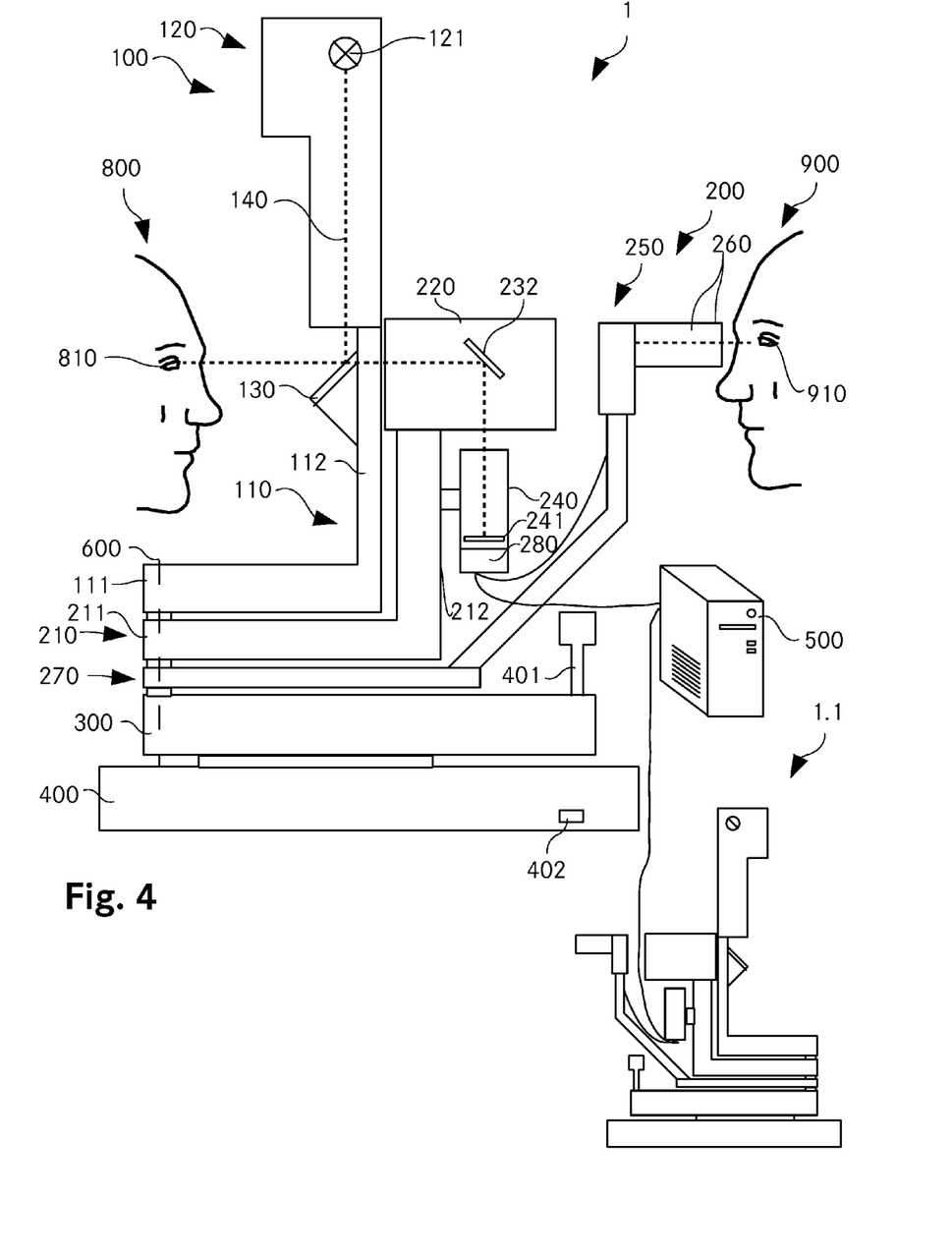
FIG. 4 shows a third embodiment of the device according to the invention in a side view.

FIG. 4 substantially corresponds to FIG. 3, wherein, in the present embodiment, a further substantially L-shaped element 270, similar to the L-shaped elements 110, 210, is additionally mounted in a pivotable fashion on the axis of rotation 600, between the slide 300 and the L-shaped element 210. Arranged in an upper region of the L-shaped element 270 there is an image rendering unit 250 with two eyepieces 260. The eyepieces 260 respectively comprise a micro-screen. The micro-screens are respectively connected to the image sensors 241 of the image recording unit 240 via a data channel; in the present embodiment via cables but a wireless transmission is also possible here. The eyepieces 260, together with the micro-screens, can also be embodied as glasses, for example as 3D video glasses, which can be detachably connected to the L-shaped element 270. The device itself can furthermore comprise a data processing unit 280, by means of which the image data can be processed. The data processing unit 280 can be designed in such a way that it is possible to execute an operating system, which can be controlled via the micro-screens of the eyepieces 260 and/or via an external additional screen 700 and a joystick, in particular the operating element 401. By means of an interface 402 it is possible to send the data to further instruments, in particular to 3D video glasses, a computer, a digital slit lamp 1 etc. In FIG. 4, a slit lamp 1.1 is illustrated in exemplary fashion as a peripheral instrument, which is connected to the device 1 via a computer 500.

According to a second aspect of the invention, the device 1 as per FIG. 4 can also be provided solely for monoscopic observation of images. To this end, the device 1 comprises an optics part 220 for recording precisely one image, and also precisely one image sensor 241 for capturing one image, and the observation unit can in this case comprise one or two eyepieces 260, by means of which the one image can be observed on the screen.

Figure 5:
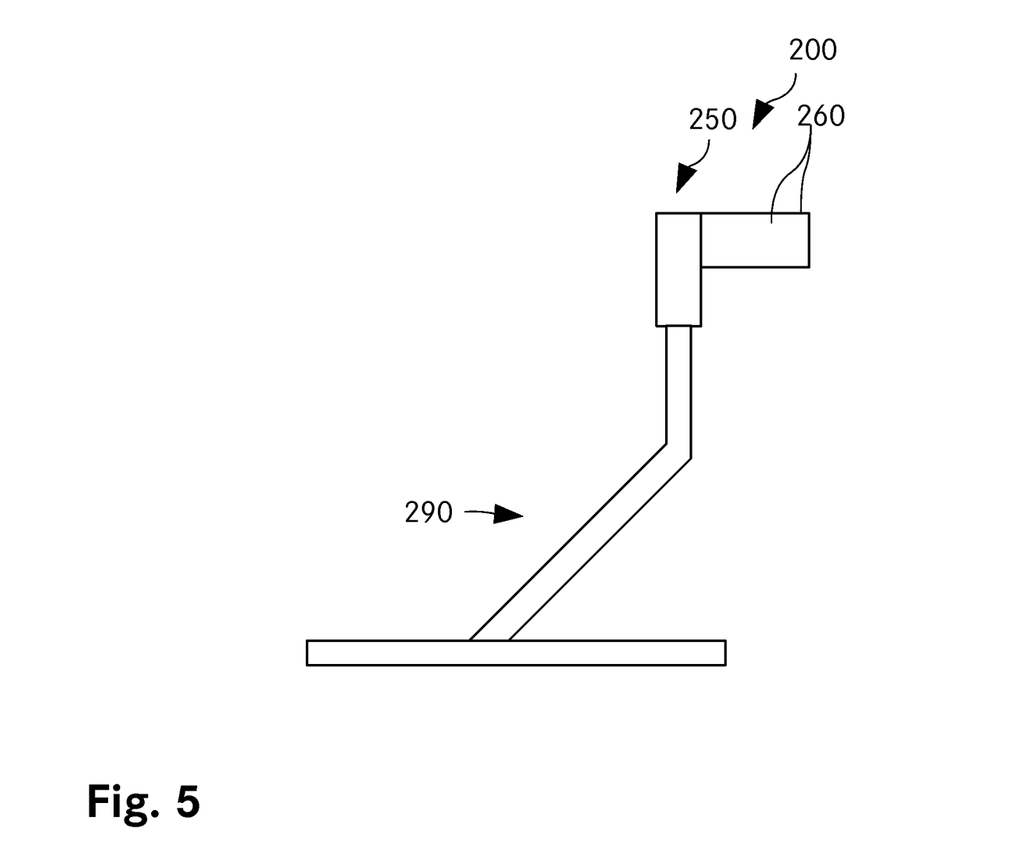
FIG. 5 shows an observation unit as an element detached from the microscope.

Finally, FIG. 5 shows an observation unit 200 as a unit detached from the microscope. In the present embodiment, the observation unit 200 is mounted on a stand 290 which can be adjusted in terms of height (not illustrated) in such a way that the operating height can be matched to the user. Here, it is understood that the stand 290 of the observation unit 200 is not restricted to the schematic illustration in FIG. 5. A person skilled in the art knows that such a stand 290 can have any design. The observation unit can be supplied with image data, either via a data cable or wirelessly. The observation unit can furthermore comprise an electronic control and an input unit (not illustrated), by means of which the micro-screens can be operated and controlled. By way of example, this can be used to adjust the brightness, the contrast and further settings of the micro-screens known to a person skilled in the art. Furthermore, provision can also be made for a processor and a storage device, by means of which the image material can be processed and stored via the operating elements. A plurality of such observation units can be coupled together in such a way that data can be interchanged amongst these. This embodiment can be advantageous, particularly in telemedicine and for training purposes.

A person skilled in the art knows that, for example, precisely one image sensor can also be provided in the present exemplary embodiments.

In conclusion, it should be noted that, according to the invention, a device for stereoscopic or monoscopic examination of an eye is developed, by means of which image material can be recorded, processed and, once again, be observed in stereoscopic or monoscopic fashion.

The invention claimed is:

1. A first device for stereoscopically examining an eye having a first optical unit for generating two first images of the eye and
    at least one first image sensors for electronic capture of the two first images; and
    a first observation unit with a first image rendering unit for displaying the two first images, and two first eyepieces for stereoscopically observing the two first images,
    wherein the first device comprises a first interface for transmitting data to a second device for stereoscopically examining an eye and for receiving data therefrom and
    wherein the second device for stereoscopically examining an eye having at least one second image sensor for electronic capturing of two second images,
    wherein the first interface can be used to receive electronically captured second images from the second device for the purpose of stereoscopically examining an eye, and wherein these second images can be rendered by means of the first image rendering unit.

2. The first device as claimed in claim 1, further comprising a data processing unit.

3. The first device as claimed in claim 2, wherein the data processing unit comprises a processor for processing data and a storage device for storing the data.

4. The first device as claimed in claim 1, wherein the electronic instrument is embodied as one or more of the following instruments:
    a) a computer;
    b) a screen.

5. The first device as claimed in claim 2, wherein the data comprise electronically captured images, time, date and/or setting data of the device.

6. The first device as claimed in claim 5, wherein the data comprise the following:
    a) a slit width;
    b) a slit height;
    c) utilized filter types;
    d) an exposure method; and/or
    e) a magnification factor.

7. The first device as claimed in claim 1, wherein the first images can, by means of the first observation unit, be selectively rendered statically as an image, dynamically as a film or dynamically as a film in real time.

8. The first device as claimed in claim 1, further comprising two first image sensors for electronic capture of the two images.

9. The first device as claimed in claim 3 wherein the data comprises the electronically captured images and/or the processed images.

10. The first device as claimed in claim 4, wherein the electronic instrument is embodied as one or more of the following instruments:
   a) a first device as claimed in claim 1;
   b) a computer network;
   c) a screen for stereoscopically observing the images.

11. The first device as claimed in claim 10, wherein the electronic instrument is embodied as an autostereoscopic display for stereoscopic rendering of the two images.

12. The first device as claimed in claim 3, wherein the data comprise electronically captured images, time, date and/or setting data of the first device.

13. The first device as claimed in claim 4, wherein the data comprise electronically captured images, time, date and/or setting data of the first device.

14. The first device as claimed in claim 1, wherein the first observation unit of the first device is embodied to be movable independently of the first optical unit.

15. The first device as claimed in claim 1, wherein at least one of the first device and the second device is a slit-lamp microscope.

16. A method for using an arrangement comprising a first device for stereoscopically examining an eye having an optical unit for generating two first images of the eye and at least one first image sensors for electronic capture of the two first images and a first observation unit with a first image rendering unit for displaying the two first images and two first eyepieces for stereoscopically observing the two first images, characterized in that the first device comprises a first interface for transmitting data to a second device for stereoscopically examining an eye and for receiving data therefrom, wherein the second device for stereoscopically examining an eye having at least one second image sensor for electronic capturing of two second images, wherein second images are electronically captured and the second images from the second device are received by the first interface for the purpose of stereoscopically examining an eye, and wherein these second images are rendered by means of the first image rendering unit.

17. An arrangement comprising a first device for stereoscopically examining an eye having a first optical unit for generating two first images of the eye and at least one first image sensors for electronic capture of the two first images and a first observation unit with a first image rendering unit for displaying the two first images and two first eyepieces for stereoscopically observing the two first images and a second device for stereoscopically examining an eye characterized in that the device comprises a first interface for transmitting data to the second device for stereoscopically examining an eye and for receiving data therefrom and wherein the second device for stereoscopically examining an eye having at least one second image sensor for electronic capturing of two second images, wherein the first interface can be used to receive electronically captured second images from the second device for the purpose of stereoscopically examining an eye, and wherein these second images can be rendered by means of the first image rendering unit.

* * * * *